(12) United States Patent
Yoon et al.

(10) Patent No.: US 11,045,119 B2
(45) Date of Patent: Jun. 29, 2021

(54) BIOSENSOR FOR MEASURING GLUCOSE COMPRISING CYTOPLASMIC FILTER

(71) Applicant: KOREA UNIVERSITY RESEARCH AND BUSINESS FOUNDATION, Seoul (KR)

(72) Inventors: Dae Sung Yoon, Seoul (KR); Do Hyung Kwon, Seoul (KR); In Su Kim, Seoul (KR); Gyu Do Lee, Namyangju-si (KR); Dong Tak Lee, Seoul (KR); Sang Won Lee, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 163 days.

(21) Appl. No.: 16/031,251

(22) Filed: Jul. 10, 2018

(65) Prior Publication Data
US 2019/0029576 A1  Jan. 31, 2019

(30) Foreign Application Priority Data

Jul. 27, 2017 (KR) .................. 10-2017-0095192
Jun. 28, 2018 (KR) .................. 10-2018-0074546

(51) Int. Cl.
*A61B 5/145* (2006.01)
*A61B 5/1468* (2006.01)
(Continued)

(52) U.S. Cl.
CPC ........ *A61B 5/14532* (2013.01); *A61B 5/1468* (2013.01); *A61B 5/72* (2013.01);
(Continued)

(58) Field of Classification Search
CPC ............ A61B 5/14517; A61B 5/14532; A61B 5/1468; A61B 5/72; A61B 2562/0295;
(Continued)

(56) References Cited

U.S. PATENT DOCUMENTS

2006/0228723 A1* 10/2006 Bradley ............... B82Y 30/00
                                                 435/6.11
2010/0185071 A1*  7/2010 Simpson ............ A61B 5/14865
                                                 600/347

(Continued)

FOREIGN PATENT DOCUMENTS

KR    10-2013-0059304    6/2013
KR    10-2017-0053189    5/2017

OTHER PUBLICATIONS

"Engineering Red-Blood-Cell-Membrane-Coated Nanoparticles for Broad Biomedical Applications" Gao et al, Mar. 2015, AiChE Journal, vol. 61, Issue 3, pp. 738-746.*

(Continued)

*Primary Examiner* — Matthew D Krcha
*Assistant Examiner* — Austin Q Le
(74) *Attorney, Agent, or Firm* — NSIP Law

(57) ABSTRACT

The present disclosure relates to a biosensor for measuring glucose in a biological sample, which contains a filter unit formed of a cytoplasmic membrane, which allows selective permeation of glucose in a biological sample. The biosensor of the present disclosure, which contains the cytoplasmic membrane filter unit allowing selective permeation of glucose in the biological sample, exhibits high glucose detection sensitivity as compared to the commercially available blood sugar measuring sensors and also exhibits high glucose detection specificity despite the addition of signal-interfering substances such as fructose, xylose, maltose, cysteine, ascorbic acid, uric acid, galactose, etc. In addition, because he cytoplasmic membrane filter unit contained in the biosensor for measuring glucose of the present disclosure is not significantly affected by the moisture in the air, it can be applied to various products such as a disposable (Continued)

blood sugar test strip or an attachable or implantable glucose measuring device.

6 Claims, 9 Drawing Sheets
(9 of 9 Drawing Sheet(s) Filed in Color)

(51) Int. Cl.
  *G01N 33/49* (2006.01)
  *A61B 5/00* (2006.01)
(52) U.S. Cl.
  CPC .......... *G01N 33/49* (2013.01); *A61B 5/14517* (2013.01); *A61B 2562/0295* (2013.01)
(58) Field of Classification Search
  CPC ........... G01N 33/49; G01N 2001/4016; G01N 2021/085; G01N 2021/075
  See application file for complete search history.

(56) References Cited

U.S. PATENT DOCUMENTS

| | | | | |
|---|---|---|---|---|
| 2010/0317092 | A1* | 12/2010 | Suzuki | A61B 5/150022 435/287.1 |
| 2014/0012115 | A1* | 1/2014 | Li | C12Q 1/54 600/347 |

OTHER PUBLICATIONS

"The SLC2 (GLUT) family of membrane transporters" Mueckler, Apr.-Jun. 2013, Molecular Aspects of Medicine, vol. 34, Issues 2-3. pp. 121-138.*

Kim, I, et al. "High Selective Glucose Sensor via Red Blood Cell Membrance and Its Glucose Transporter-1", proceedings of the *39th Annual International Conference of the IEEE Engineering in Medicine and Biology Society*, Jul. 11 to 15, 2017, Jeju Island, Korea (3 pages in English).

* cited by examiner

BIOSENSOR FOR MEASURING GLUCOSE COMPRISING CYTOPLASMIC FILTER

CROSS-REFERENCE TO RELATED APPLICATIONS

This application claims, under 35 U.S.C. § 119, the priority of Korean Patent Application No. 10-2017-0095192 filed on 27 Jul. 2017 and No. 10-2018-0074546 filed on 28 Jun. 2018, in the Korean Intellectual Property Office, the disclosure of which is incorporated herein by reference in its entirety.

The Research No. NRF-2018M3C1B7020722 was supported by the National Research Foundation of Korea (NRF) Grant funded by the Korean Government (MSIP). The Research No. 10079316 was also supported by the Ministry of Trade, Industry & Energy (MOTIE, Korea) under Industrial Technology Innovation Program. There is no property interest of the Korean Government in any aspect of this invention.

TECHNICAL FIELD

The present disclosure relates to a biosensor for measuring glucose, more particularly to a biosensor for measuring glucose in a biological sample, which contains a filter unit formed of a cytoplasmic membrane, which allows selective permeation of glucose in a biological sample.

BACKGROUND

Diabetes is a disease occurring due to improper carbohydrate metabolism, which disturbs normal use of glucose absorbed in the body. It can cause various complications due to very high blood sugar levels. It is largely classified into three types. Type 1 diabetes is insulin-dependent diabetes wherein pancreatic cells lose the function of synthesizing or secreting insulin due to autoimmune responses. Type 2 diabetes is non-insulin-dependent diabetes occurring due to insulin resistance, improper insulin secretion, etc. Gestational diabetes may occur in pregnant women. However, type 1 diabetes and gestational diabetes are not common and most of diabetes is type 2 diabetes, which accounts for 90-95% of all diabetic diseases occurring in developed countries.

Due to the eating habits, psychological stress and lifestyles of modern people, the number of the patients suffering from the metabolic disease diabetes is increasing continuously. As of 2015, an estimated 415 million people, which corresponds to about 9% of the world population, had diabetes. It is estimated that the number of the patients will increase to 642 million, corresponding to about 10% of the world population, in 2040. The global cost of diabetes is 673 billion dollars, which accounts for 12% of the total healthcare market (International Diabetes Federation).

The patients suffering from diabetes should be regularly treated with insulin. For accurate medication of insulin, a blood sugar self-monitoring device called a glucose sensor is used. Use of such a device is very important in determining the administration time and dosage of insulin and, therefore, is an important part in the treatment of diabetes. Globally, about 400 million patients use 5-10 sensors every day. This reflects that the self-monitoring of blood sugar is important for diabetic patients.

As the blood sugar monitoring devices, those using an electrochemical method are generally used to provide high precision. In particular, a technique of using enzymes such as glucose oxidase (GOx) or glucose dehydrogenase to measure the glucose in blood by generating an electrical signal is commercialized. When the glucose in blood encounters the enzymes, an electrical signal is generated as the glucose is oxidized and the electron transport material (water or a coenzyme) is reduced through oxidation-reduction reactions. The glucose level in a solution or blood is measured in short time by measuring the intensity of the electrical signal generated as the reduced electron transport material encounters an electrode. However, the enzyme-based glucose sensor has many problems in terms of enzyme stability, oxygen dependence, role of a mediator and enzyme leaching. GOx rapidly loses its activity at pH 4 or lower or at pH 7 or higher and is denatured quickly at 70° C. or above. In addition, high and low humidity are unfavorable for storage and use of the sensor.

Although devices measuring blood sugar noninvasively are emerging recently, they show significantly low glucose detection efficiency as compared to the blood sugar measuring devices requiring blood or urine sampling. The glucose measuring devices requiring blood or urine sampling also show decreased efficiency and accuracy of glucose detection due to signal-interfering particles. For this reason, various circumventing methods such as detecting glycated hemoglobin have been used to measure blood sugar rather than directly measuring the glucose concentration. The inventors of the present disclosure have studied on a method for detecting glucose directly and diagnosing diabetes with high glucose detection efficiency and accuracy. As a result, they have invented a biosensor for measuring glucose in a biological sample using a cytoplasmic membrane filter.

REFERENCES OF THE RELATED ART

Patent Documents (Patent document 1) Korean Patent Publication No. 10-2013-0059304.

(Patent document 2) Korean Patent Publication No. 10-2017-0053189.

SUMMARY

The present disclosure is directed to providing a biosensor for measuring glucose in a biological sample, which contains a filter unit formed of a cytoplasmic membrane, a kit for measuring glucose in a biological sample containing the biosensor and a method for measuring a glucose level in a biological sample using the biosensor.

In an aspect, the present disclosure provides a biosensor for measuring glucose, containing a filter unit formed of a cytoplasmic membrane, wherein the filter unit allows selective permeation of glucose in a biological sample.

In another aspect, the present disclosure provides a kit for measuring glucose in a biological sample, which contains the biosensor.

In another aspect, the present disclosure provides a method for measuring a glucose level in a biological sample, which includes a step of contacting a biological sample to the biosensor.

The biosensor of the present disclosure, which contains a filter unit formed of a cytoplasmic membrane, which allows selective permeation of glucose in a biological sample, exhibits high glucose detection sensitivity and, at the same time, high detection specificity for glucose in a biological sample despite the addition of signal-interfering substances such as ascorbic acid, uric acid or galactose as compared to the commercially available blood sugar measuring sensors. In addition, the biosensor for measuring glucose of the present disclosure can be applied to various products such as a disposable blood sugar test strip or an attachable or implantable glucose measuring device because the filter unit formed of a cytoplasmic membrane contained in the biosensor for measuring glucose of the present disclosure is not greatly affected by the change in conditions such as moisture.

BRIEF DESCRIPTION OF DRAWINGS

The patent or application file contains a least one drawing executed in color. Copies of this patent or patent application publication with color drawing(s) will be provided by the Office upon request and payment of the necessary fee.

In FIG. 2, (iii) is a filter unit, (ii) is a sensor unit and (i) is a measuring unit. A reading unit (not shown in the figure) is connected from the rear side of the sensor to an electrochemical device (potentiostat) via a circuit.

FIG. 4A shows a result for a test group wherein a cytoplasmic membrane filter is coated and FIG. 4B shows a result for a control group.

FIG. 9A: ascorbic acid (AA), FIG. 9B: uric acid (UA), FIG. 9C: galactose (GA), FIG. 9D: AA, UA and GA.

DETAILED DESCRIPTION OF EMBODIMENTS

Figure 1:
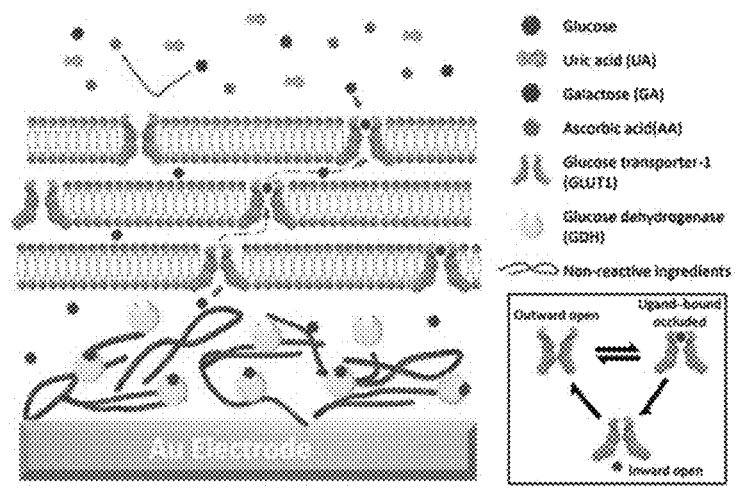
FIG. 1 shows the principle of a biosensor for measuring glucose of the present disclosure.

Hereinafter, the present disclosure is described in detail.

In an aspect, the present disclosure provides a biosensor for measuring glucose, containing a filter unit formed of a cytoplasmic membrane, wherein the filter unit allows selective permeation of glucose in a biological sample.

In the present disclosure, the 'biosensor' refers to an analytical device used for the detection of an analyte using the biological function. In general, it has a sensitive biological element, a transducer or detector element and a biosensor reader device. In the present disclosure, the biosensor may be interpreted as a glucose sensor.

In the present disclosure, the biosensor may be applied to various products such as a disposable blood sugar test strip or an attachable or implantable glucose measuring device for the purpose of glucose measurement without limitation.

In the present disclosure, the biosensor contains a filter unit formed of a cytoplasmic membrane, which allows selective permeation of glucose in a biological sample, a sensor unit recognizing the permeated glucose and a reading unit reading a signal of the recognized glucose and may further contain a measuring unit converting the recognized glucose into a signal between the sensor unit and the reading unit.

In the present disclosure, the 'biological sample' refers to an analyte containing glucose and includes blood, urine, sweat, tears, etc. Specifically, it may be blood, although not being limited thereto.

In the present disclosure, the 'filter unit' refers to a unit which purifies the biological sample and serves to allow selective permeation of glucose in the biological sample. The 'filter unit' according to the present disclosure is formed of a 'cytoplasmic membrane'. The cytoplasmic membrane may be derived from red blood cells or cancer cells, although not being limited thereto.

Specifically, the cytoplasmic membrane may contain a membrane protein and a glucose transporter (GLUT) protein.

The glucose transporter protein is a protein that introduces glucose into a cell through the cytoplasmic membrane. It is a transporter that facilitated diffusion-type transporter driven by the difference in glucose concentration inside and outside the cell. It may be GLUT1, GLUT2, GLUT3, GLUT4, etc., specifically GLUT1, although not being limited thereto.

The thickness of the filter unit may be optimized by controlling the kind of the cytoplasmic membrane and the biological sample for selective permeation of the glucose stable transfer of signals.

The filter unit may be formed by coating a cytoplasmic membrane on a biosensor. In an exemplary embodiment of the present disclosure, it was confirmed that the thickness of the cytoplasmic membrane increases with the concentration of the red blood cell membrane (FIG. 5(a)).

In the present disclosure, 'the concentration of the red blood cell membrane' is represented by the volume of the red blood cell membrane contained in 1 mL of a 0.1 M phosphate buffer (% (v/v)).

In the present disclosure, the filter unit may have a thickness of specifically 100-300 nm, more specifically 150-250 nm, although not being limited thereto. If the thickness of the filter unit is smaller than 100 nm, the possibility of molecules other than glucose passing through the cytoplasmic membrane is increased. And, if it exceeds 300 nm, the passage of the glucose through the cytoplasmic membrane may be retarded.

Figure 5:
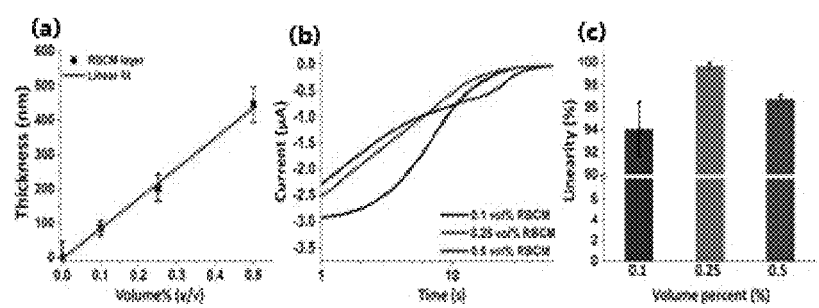
FIG. 5 shows a result of investigating signal transfer efficiency depending on the filter unit thickness of a biosensor. (a) shows a result of investigating the correlation between the concentration of red blood cell membrane and the filter unit thickness. (b) shows a result of investigating the correlation between the concentration of red blood cell membrane and current. (c) shows a result of analyzing linearity from the result of b between 3 and 10 seconds.

In an exemplary embodiment of the present disclosure, it was confirmed that the change in signal intensity per unit time in the early stage of reaction is the highest when the filter unit with a thickness of about 220 nm is formed by coating 0.25% (v/v) red blood cell membrane (see FIG. 5).

When the biological sample is blood, the thickness may be 100-300 nm, specifically 150-250 nm, although not being limited thereto. For biological samples of other concentration ranges such as urine, tears, etc., the thickness may be optimized otherwise.

In the present disclosure, the 'sensor unit' refers to a unit recognizing the glucose in the biological sample that has been permeated by the filter unit. Specifically, the sensor unit may contain an enzyme such as glucose oxidase, glucose dehydrogenase (GDH), glucose hexokinase, cholesterol oxidase, glutamic oxaloacetic transaminase (GOT), glutamic pyruvic transaminase (GPT), etc. In addition, it may further contain pyrroloquinoline quinone (PQQ) as a coenzyme. Any enzyme that uses glucose as a substrate may be contained without limitation. When the enzymes contained in the sensor unit encounter the glucose in blood, an electrical signal is generated as the glucose is oxidized and the enzymes are reduced. The intensity of the generated electrical signal is measured as the reduced enzymes encounter an electrode.

In the present disclosure, the 'measuring unit' is a unit which converts the recognized glucose into a signal between the sensor unit and the reading unit. For example, the glucose is converted into a signal in the form of an electron ($e^-$) through a series of oxidation and reduction reactions between the enzymes in the sensor unit and an electron transport mediator. The generated oxidation potential may be applied to the electrode to generate a current.

The electron transport mediator may be ferrocene, a ferrocene derivative, quinone, a quinone derivative, an organic conducting salt, a viologen, potassium hexacyanoferrate(III), potassium ferricyanide, potassium ferrocyanide, hexaammineruthenium(III) chloride, etc., although not being limited thereto. The electrode may be a gold (Au), silver (Ag) or copper (Cu) electrode. Specifically, a gold electrode may be used for accuracy of the electrical signal, although not being limited thereto.

In the present disclosure, the 'reading unit' is a unit which reads the signal of the recognized glucose. For example, it may provide information by displaying the current signal converted from the glucose as a numerical value.

In another exemplary embodiment of the present disclosure, the glucose itself is provided as a numerical information without using the measuring unit.

In another aspect, the present disclosure provides a kit for measuring glucose, which contains the biosensor.

The kit according to the present disclosure may further contain, in addition to the biosensor of the present disclosure, a tool which helps blood sampling, urine sampling, etc. for more effective measurement of glucose. The kit may contain an external package and the external package may contain instructions about the use of the constituent elements.

In another aspect, the present disclosure provides a method for measuring a glucose level in a biological sample, which includes a step of contacting a biological sample to the biosensor.

Diabetes may be diagnosed or prognosed by measuring glucose concentration according to the method.

In another aspect, the present disclosure provides a method for preparing a biosensor for measuring glucose, which includes:

(1) a step of obtaining a cytoplasmic membrane by centrifuging a cell;

(2) a step of preparing the cytoplasmic membrane obtained in the step (1) into a vesicle state by sonicating or extruding the same; and (3) a step of coating the cytoplasmic membrane in the vesicle state prepared in the step (2) on a sensor unit.

Each step is described in more detail.

In the step (1), substances other than the cytoplasmic membrane containing a membrane protein, i.e., organelles or hemoglobins, are removed from the cell. The centrifugation may be repeated to improve the cytoplasmic membrane isolation efficiency.

In the step (2), the cytoplasmic membrane is prepared into a vesicle state by sonicating or extruding the same for effective coating of the cytoplasmic membrane. The sonication may be performed for about 20-60 minutes, specifically about 30 minutes, although not being limited thereto. The vesicle prepared through the sonication or extrusion may have a diameter of specifically 70-200 nm, although not being limited thereto.

In the step (3), the cytoplasmic membrane in the vesicle state is coated on a sensor unit so that the cytoplasmic membrane in the vesicle state can serve as a filter unit. The cytoplasmic membrane in the vesicle state may be coated to a concentration of 0.1-0.5 vol %, although not being limited thereto.

Description of the matters described above will be omitted to avoid redundancy. The terms not defined otherwise in the present disclosure will have the meaning commonly used in the art to which the present disclosure belongs.

Hereinafter, the present disclosure will be described in more detail through examples and test examples. However, the following examples and test examples are for illustrative purposes only and not intended to limit the scope of this disclosure.

Example 1. Preparation of Biosensor Containing Filter Unit Formed of Cytoplasmic Membrane Containing Membrane Protein 1-1. Isolation of Cytoplasmic Membrane 1-1-1. Isolation of Cytoplasmic Membrane from Red Blood Cells Blood (whole blood) was sampled using a tube treated with EDTA (ethylenediaminetetraacetic acid) and centrifuged at 4° C. and 500 g for 5 minutes. After removing the supernatant which contains relatively light plasma and white blood cells, the lower layer containing red blood cells only was separated. After adding 1 mL of 1×PBS (pH 7.4, Gibco) to the separated lower layer and centrifuging at 500 g for 5 minutes, the supernatant not containing the red blood cells was removed. The red blood cells were purified by repeating this washing process 3 times. Then, the red blood cells were immersed in 0.25×PBS for 20 minutes to induce hemolysis.

In order to separate only the membrane protein and the red blood cell membrane from the PBS solution in which the red blood cell membrane, the membrane protein and hemoglobin existed together, centrifugation was performed further at 1000 g for 5 minutes. After removing the supernatant, the red blood cell membrane containing the membrane protein, which settled down with a light pink color was obtained. For further purification, 1 mL of 1×PBS was added and centrifugation was performed at 1000 g for 5 minutes. This procedure was repeated 3 times.

1-1-2. Isolation of Cytoplasmic Membrane from Cancer Cells

Cancer cells MDA-MB-231 acquired from the Korean Cell Line Bank were mixed with a culture medium PBS (pH 7.4, Gibco) and centrifuged at 4° C. and 500 g for 5 minutes. The supernatant was removed from the cells which settled down in the lower layer and formed a colony. After adding 1 mL of 1×PBS (pH 7.4, Gibco) and centrifuging at 500 g for 5 minutes, the supernatant was removed. This purification process was repeated 3 times. Then, the cells were immersed in 0.25×PBS for 20 minutes in order to induce the separation of the cytoplasmic membrane. In order to separate the membrane protein and the red blood cell membrane from the PBS solution in which the cytoplasmic membrane, the membrane protein and cell organelles existed together, centrifugation was performed further at 1000 g for 5 minutes. After removing the supernatant, the cytoplasmic membrane containing the membrane protein, which settled down in the lower layer was obtained. For further purification, 1 mL of 1×PBS was added and centrifugation was performed at 1000 g for 5 minutes. This procedure was repeated 3 times.

1-2. Coating of Cytoplasmic Membrane on Sensor Unit of Biosensor 2.5 μL of the purified cytoplasmic membrane containing the membrane protein isolated in Example 1-1-1 or 1-1-2 was dissolved in 1 mL of distilled water and diluted 400-fold. Then, the cytoplasmic membrane was prepared into a vesicle state with a diameter of about 170 nm by sonicating for 30 minutes. Then, after separating a glucose sensor from a commercially available product (Accu-Chek Inform II System, Roche Diagnostics, USA), 25 μL of the cytoplasmic membrane in the vesicle state was coated on the glucose sensor so that the enzyme portion (about 33 mm$^2$), i.e., the sensor unit, could be enclosed enough. Heating was performed for 5 minutes in a drying oven set to 50° C. so that the cytoplasmic membrane could be sufficiently coated on the sensor without enzyme damage. 50 minutes later, the sensor was left at room temperature for 50 minutes.

Figure 2:
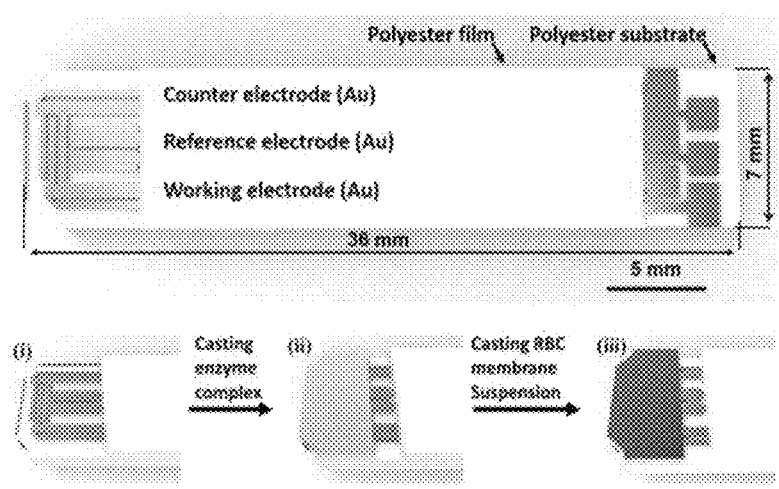
FIG. 2 schematically shows the structure of a biosensor for measuring glucose of the present disclosure.
Figure 3:
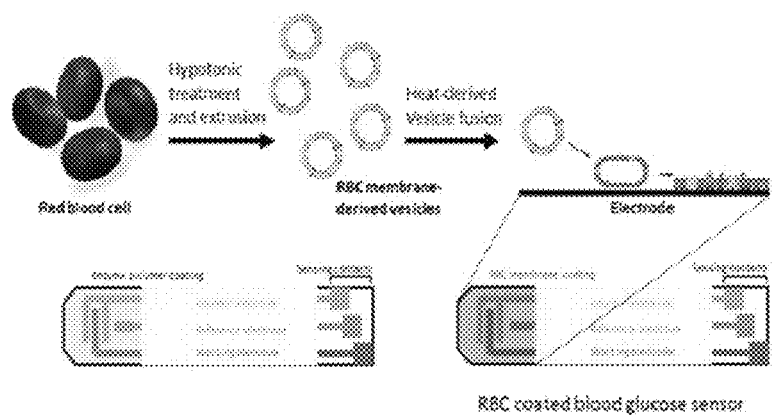
FIG. 3 schematically shows a process of isolating a cytoplasmic membrane from red blood cells and coating it on a sensor unit in order to prepare a biosensor for measuring glucose of the present disclosure.

The principle and structure of the biosensor according to the present disclosure are shown in FIG. 1 and FIG. 2, respectively. In addition, the preparation biosensor process described above is schematically shown in FIG. 3.

Test Example 1. Confirmation of Cytoplasmic Membrane Coating on Biosensor Through SEM Analysis The sensor unit of the cytoplasmic membrane-coated biosensor prepared in Example 1-2 was analyzed by SEM in order to confirm whether the cytoplasmic membrane containing the membrane protein was coated normally. In addition, SEM analysis was conducted for the same portion of a product (Accu-Chek Inform II System, Roche Diagnostics, USA) not coated with the cytoplasmic membrane of the present disclosure as a control group. The result for the test group is shown in FIG. 4A and the result for the test control group is shown in FIG. 4B.

Figure 4A:
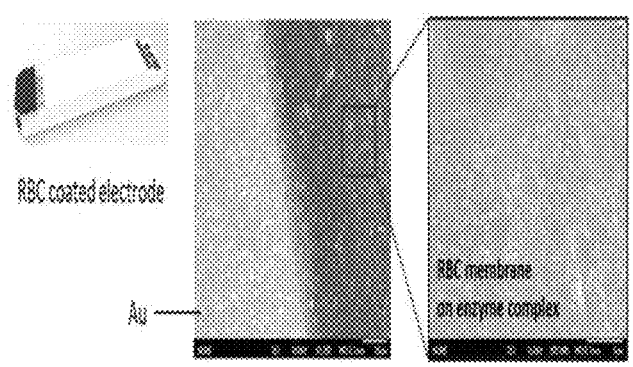
FIGS. 4A and 4B show a result of investigating the surface of a biosensor for measuring glucose through SEM analysis.
Figure 4B:
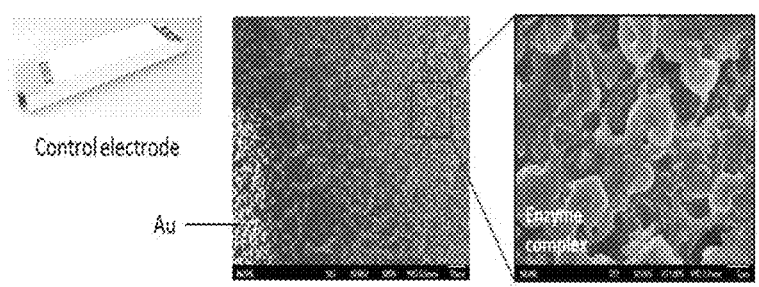

As seen from FIGS. 4A and 4B, it was confirmed that the cytoplasmic membrane was coated normally on the sensor unit of the biosensor.

Test Example 2. Confirmation of Current Depending on Thickness of Red Blood Cell Membrane-Coated Filter Unit In order to investigate the optimum filter unit thickness of the biosensor of the present disclosure, the red blood cell membrane obtained in Example 1-1-1 was coated on the sensor unit of the biosensor at concentrations from 0 to 0.5% (v/v). More specifically, the % (v/v) value was calculated based on the volume of the red blood cell membrane contained in 1 mL of a 0.1 M phosphate buffer. For example, 0.25% (v/v) means that 2.5 μL of the red blood cell membrane obtained in Example 1-1-1 was added to 1 mL of the phosphate buffer. The thickness of the filter unit depending on the concentration of the red blood cell membrane was measured using a stylus profiler (Alpha-step D100, KLA-Tencor). The result is shown in FIG. 5(a).

As seen from FIG. 5(a), the thickness of the filter unit was increased with the concentration of the red blood cell membrane.

In addition, the current in the biosensor prepared using the red blood cell membrane with a concentration of 0.1% (v/v), 0.25% (v/v) or 0.5% (v/v) was analyzed using the electrochemical device potentiostat (VersaSTAT 3) and linearity was analyzed between 1 and 10 seconds. For this, after dropping 30 μL of the test solution onto the sensor unit (on the cytoplasmic membrane filter), current was measured with 0.5-second intervals while applying a voltage of −0.3 V. The result is shown in FIG. 5(b) and FIG. 5(c). FIG. 5(b) shows a result of observing the change of the electrical signal for each concentration from 1 to 60 seconds and FIG. 5(c) shows a result of analyzing linearity between 1 and 10 seconds.

As seen from FIG. 5(b) and FIG. 5(c), the signal was stably transferred when the red blood cell membrane at a concentration of 0.25% (v/v) (thickness of about 220 nm) was used. For a glucose sensor, it is particularly important to obtain the result fast. As seen from FIG. 5(c), the change in the signal intensity per unit time in the early stage was the highest when the blood cell membrane at a concentration of 0.25% (v/v) (thickness of about 220 nm) was used.

Test Example 3. Confirmation of Current Depending on Thickness of Cancer Cell Membrane-Coated Filter Unit In order to investigate the optimum filter unit thickness of the biosensor of the present disclosure, the cancer cell membrane obtained in Example 1-1-2 was coated on the sensor unit of the biosensor at concentrations from 0 to 5% (v/v). More specifically, the % (v/v) value was calculated based on the volume of the cancer cell membrane contained in 1 mL of a 0.1 M phosphate buffer. For example, 0.5% (v/v) means that 5.0 μL of the cancer cell membrane obtained in Example 1-1-2 was added to 1 mL of the phosphate buffer. The thickness of the filter unit depending on the concentration of the cancer cell membrane was measured using a stylus profiler (Alpha-step D100, KLA-Tencor). It was confirmed that the thickness of the filter unit was increased with the concentration of the cancer cell membrane.

Figure 6:
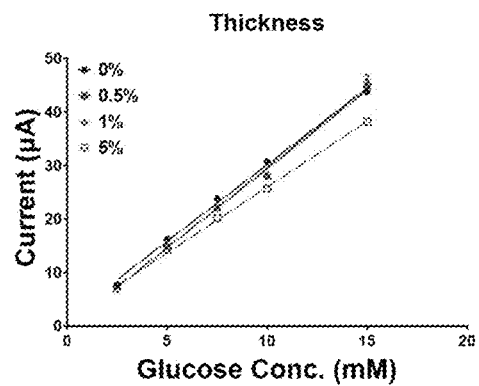
FIG. 6 shows the relationship between the thickness of cancer cell membrane and current.

In addition, current was analyzed for the biosensor coated with the cancer cell membrane with a concentration of 0.5% (v/v) (thickness: 450±40 nm), 1% (v/v) (thickness: 900±53 nm) or 5% (v/v) (thickness: 4700±102 nm) using the electrochemical device potentiostat (VersaSTAT 3) while varying the glucose concentration from 0 to 20 mM. FIG. 6 shows a result of investigating the current depending on the thickness of the cancer cell membrane. When the cancer cell membrane was too thick (5%), the signal intensity was low. When the cancer cell membrane was coated with a concentration of 0.5-1%, the electrical signal was transferred effectively as compared to the uncoated biosensor.

Figure 7:
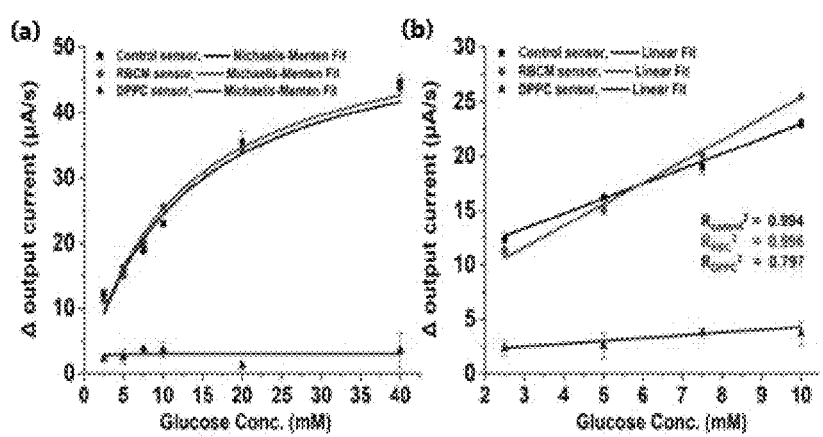
FIG. 7 shows a result of investigating the glucose detection sensitivity of a biosensor depending on the change in glucose concentration. (b) shows a result of magnifying a portion (2.5-10 mM) of (a).

Test Example 4. Confirmation of Glucose Detection Efficiency Depending on Presence of Filter Unit Formed of Red Blood Cell Membrane Containing Membrane Protein and Glucose Concentration in Sample The glucose detection efficiency of the biosensor of the present disclosure was comparatively analyzed depending on the presence of the filter unit formed of the cytoplasmic membrane containing the membrane protein. Specifically, Accu-Chek Performa (control sensor, Accu-Chek) and Accu-Chek Performa coated with a GLUT1-free artificial phospholipid membrane (DPPC sensor) were used as control groups and, as a test group, a biosensor coated with the red blood cell membrane containing the membrane protein of the present disclosure (RBCM sensor) was used. After adding 30 μL of a 0-40 mM glucose (dissolved in pH 7.4 phosphate buffer, Sigma) sample, current was measured while applying a voltage of −0.3 V and the change in signal was recorded between 3 and 7 seconds. The result is shown in FIG. 7. FIG. 7(b) shows a result of magnifying a portion (2.5-10 mM) of FIG. 7(a) in order to emphasize the range where the blood sugar level is higher than that of clinically healthy people (3.5-7 mM). In the figures, the x-axis represents the glucose concentration and the y-axis represents the change in electrical signal between 3 and 7 seconds.

As seen from FIG. 7, when the biosensor was coated with the artificial phospholipid membrane, the purification efficiency of the filter unit could be improved but the change in glucose concentration could not be measured sensitively because the movement of glucose was restricted. In contrast, when the biosensor was coated with the cytoplasmic membrane according to the present disclosure, the limit of detection (LOD) in serum was excellent as compared to the uncoated biosensor. Specifically, whereas the uncoated biosensor had an LOD of 1.34 mM in the phosphate buffer, the limit of detection in serum was decreased to about half with an LOD of 2.51 mM. In contrast, the biosensor coated with the red blood cell membrane of the present disclosure had an LOD of 1.06 mM in the phosphate buffer and 1.11 mM in the serum, which reveals that the LOD is not greatly affected by the proteins and ions in the serum.

Figure 8:
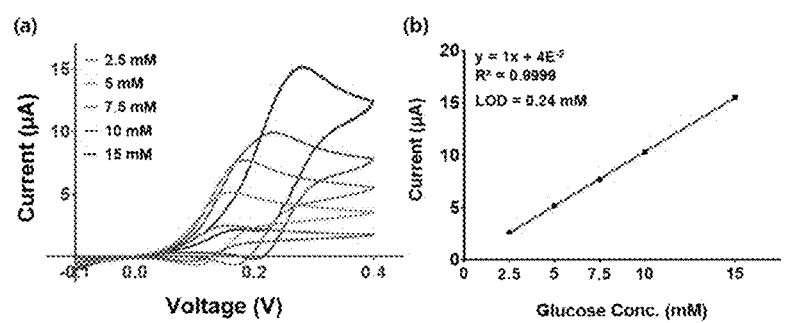
FIG. 8 shows a result of measuring current by cyclic voltammetry (CV) for a biosensor coated with cancer cell membrane (2.5%) according to the present disclosure while varying glucose concentration (a) and the relationship between current and glucose concentration for the peak currents in the CV measurement (b). The linear fitting result and related equations are given in the graph.

Test Example 5. Confirmation of Detection Sensitivity of Cancer Cell Membrane-Coated Biosensor Depending on Glucose Concentration in Sample In order to investigate the glucose detection efficiency of the biosensor according to the present disclosure, the glucose detection efficiency of the biosensor formed of the cancer cell membrane containing the membrane protein of the present disclosure was analyzed depending on the change in glucose concentration in the sample. Specifically, after adding 30 μL of a 0-20 mM of glucose (dissolved in pH 7.4 phosphate buffer, Sigma) sample to 2.5% of the cancer cell membrane-coated biosensor (RBCM sensor) according to the present disclosure, current was measured by cyclic voltammetry (CV) while applying a voltage of −0.1 to 0.4 V. The result is shown in FIG. 8 (a). FIG. 8 (b) shows the relationship between current and glucose concentration for the peak currents in the CV measurement. In the figures, the x-axis represents glucose concentration and the y-axis represents change in electrical signal between 3 and 7 seconds. The linear fitting result and related equations are given in the graph. The limit of detection was calculated to be 0.24 mM.

Whereas the uncoated biosensor had an LOD of 1.34 mM in the phosphate buffer, the cancer cell membrane-coated biosensor of the present disclosure showed a remarkably improved limit of detection with an LOD of 0.24 mM.

Figure 9A:
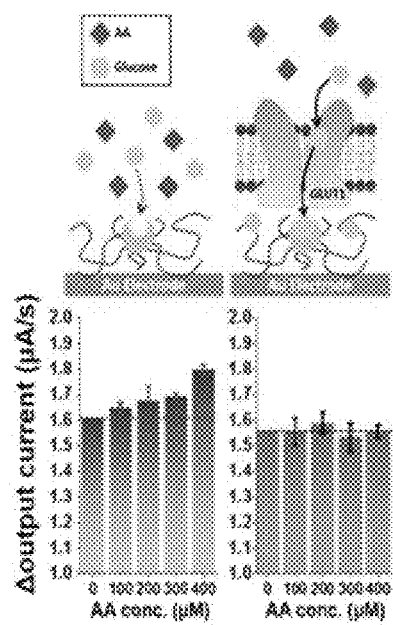
FIGS. 9A-9D show a result of investigating the glucose detection specificity of a biosensor depending on the addition of signal-interfering substances.
Figure 9B:
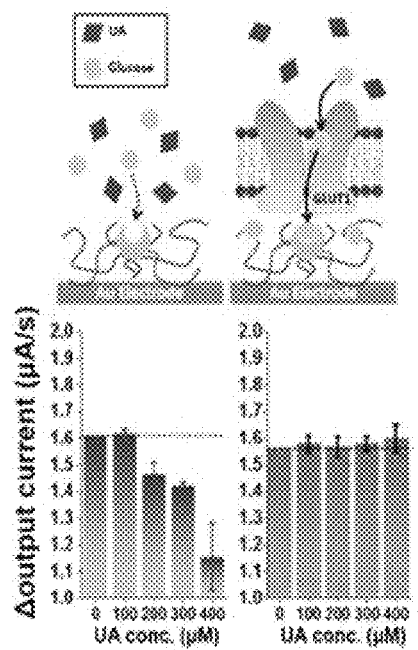
Figure 9C:
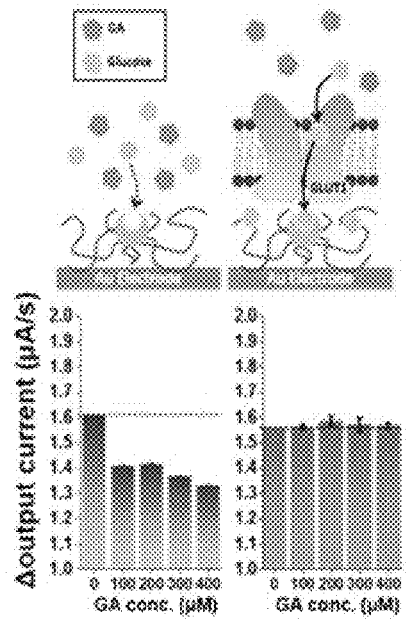

Test Example 6. Confirmation of Glucose Detection Specificity Red Blood Cell Membrane-Coated Biosensor of the Present Disclosure Depending on Addition of Signal-Interfering Substances In order to investigate the glucose detection specificity of the red blood cell membrane-coated biosensor according to the present disclosure, 5 mM glucose (corresponding to average glucose concentration in human) and the signal-interfering substance ascorbic acid (AA), uric acid (UA) or galactose (GA) at different concentrations were added to a sample and the change in current was measured. Specifically, after adding 30 μL of the sample to the sensor, current was measured while applying a voltage of −0.3 V and the change in signal between 3 and 7 seconds was recorded. The result when AA was added additionally is shown in FIG. 9A, the result when UA was added additionally is shown in FIG. 9B and the result when GA was added additionally is shown in FIG. 9C. The result when the signal-interfering substance was absent is represented as a dotted line.

Figure 9D:
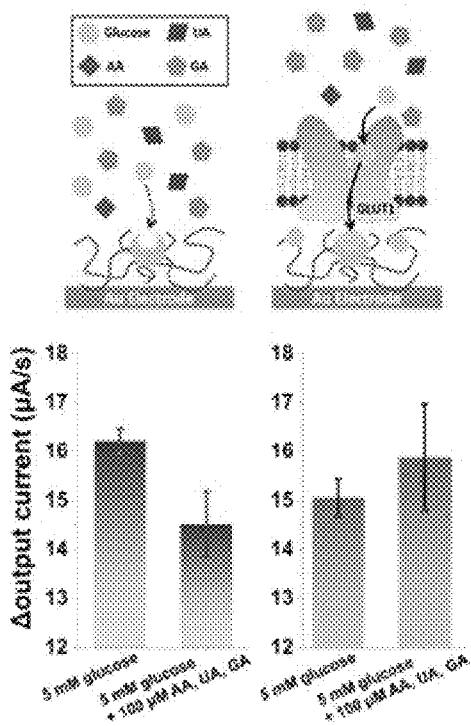

In addition, the change in current was measured after adding the signal-interfering substances AA, US and GA at 100 μM to the sample containing 5 mM glucose. The result is shown in FIG. 9D. As a control group, Accu-Chek Performa not coated with the cytoplasmic membrane was used.

As seen from FIGS. 9A-9D, whereas the control group showed increased difference from the normal value as the concentration of the signal-interfering substance was increased, the biosensor coated with the cytoplasmic membrane of the present disclosure could specifically detect glucose only without being significantly affected by the addition of the signal-interfering substance. That is to say, when the red blood cell membrane containing the membrane protein is used as a filter according to the present disclosure, glucose present in the sample can be detected with high sensitivity because not only monosaccharides or disaccharides but also polysaccharides other than glucose present in the sample cannot pass through the filter.

Figure 10:
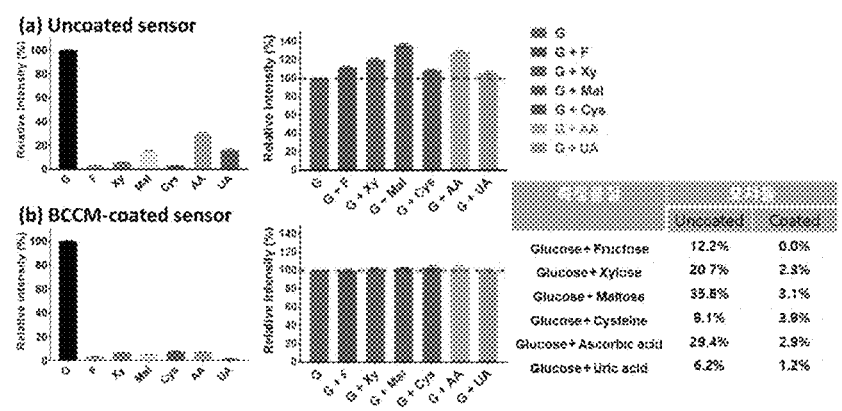
FIG. 10 shows a result of measuring the signals of substances other than glucose (interfering substances) for a biosensor not coated with cancer cell membrane (a) and a biosensor coated with cancer cell membrane (b) (G: glucose 5 mM, F: fructose 5 mM, Xy: xylose 5 mM, Mal: maltose 1 mM, Cys: cysteine 1 mM, AA: ascorbic acid 1 mM, UA: uric acid 0.5 mM).

Test Example 7. Confirmation of Glucose Detection Specificity of Cancer Cell Membrane-Coated Biosensor of the Present Disclosure Depending on Addition of Signal-Interfering Substances In order to investigate the glucose detection specificity of the cancer cell membrane-coated biosensor according to the present disclosure, 5 mM glucose (corresponding to average glucose concentration in human) and the signal-interfering substance fructose, xylose, maltose, cysteine, ascorbic acid (AA) or uric acid (UA) at different concentrations were added to a sample and the change in current was measured. The result is shown in FIG. 10. Specifically, after adding 30 µL of the sample to the sensor, current was measured while applying a voltage of −0.3 V and the change in signal between 3 and 7 seconds was recorded. The signals for the molecules are shown on the left side and the results for the 5 mM glucose with the molecules added are shown on the right side. The result when the signal-interfering substance was absent is represented as a dotted line. As a control group, Accu-Chek Performa not coated with the cytoplasmic membrane was used.

As seen from FIG. 10, whereas the control group showed increased difference from the normal value as the concentration of the signal-interfering substance was increased, the cancer cell membrane-coated biosensor of the present disclosure could specifically detect glucose only without being significantly affected by the addition of the signal-interfering substance. That is to say, when the cancer cell membrane containing the membrane protein is used as a filter according to the present disclosure, glucose present in the sample can be detected with high sensitivity because not only monosaccharides or disaccharides but also polysaccharides other than glucose present in the sample cannot pass through the filter.

Test Example 8. Confirmation of Glucose Detection Sensitivity of Biosensor of the Present Disclosure Depending on Addition of Glucose to Serum In order to investigate the detection sensitivity of the biosensor according to the present disclosure, human serum acquired from Sigma was used as a sample. After adding glucose at different concentrations, the change in current was measured for the biosensor of the present disclosure depending on the addition amount of the glucose. Specifically, after adding 30 µL of the sample to the red blood cell membrane (RBCM)-coated biosensor, current was measured while applying a voltage of −0.3 V and the change in signal between 3 and 7 seconds was determined. As a control group, Accu-Chek Performa not coated with the cytoplasmic membrane was used. The result is shown in FIG. 11.

Figure 11:
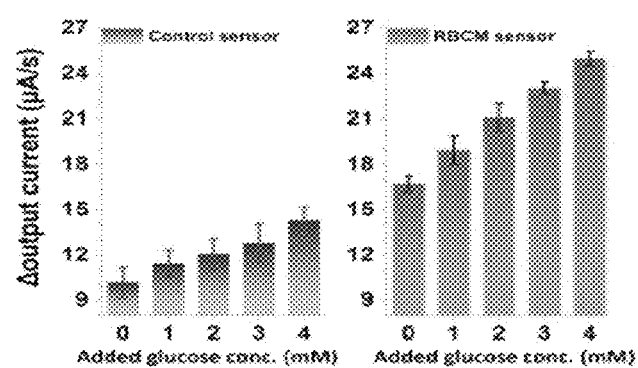
FIG. 11 shows a result of investigating the glucose detection sensitivity of a biosensor depending on the increase in glucose concentration in serum.

As seen from FIG. 11, the current was increased as the amount of glucose added to the serum was increased and it was confirmed that the red blood cell membrane-coated biosensor of the present disclosure can detect glucose with remarkably higher sensitivity as compared to the control group. This means that, although the presence of the substances exhibiting electrical signals themselves or the substances interfering the enzyme-glucose interaction in blood leads to slightly decreased glucose detection efficiency for the existing biosensor not coated with the cytoplasmic membrane, the use of the red blood cell membrane containing the membrane protein according to the present disclosure as a filter allows detection of glucose with high sensitivity even when the serum itself is used as a sample.

Test Example 9. Comparison of Glucose Detection Sensitivity of Red Blood Cell Membrane (RBCM)-Coated Biosensor and Cancer Cell Membrane (CCM)-Coated Biosensor In order to compare the glucose detection sensitivity of the red blood cell membrane (RBCM)-coated biosensor and the cancer cell membrane (CCM)-coated biosensor, human serum acquired from Sigma was used as a sample. After adding glucose at different concentrations, the signal intensity was measured for the red blood cell membrane (RBCM)-coated biosensor and the cancer cell membrane (CCM)-coated biosensor. Specifically, after adding 30 µL of the sample to the red blood cell membrane (RBCM)-coated biosensor or the cancer cell membrane (CCM)-coated biosensor, the signal intensity was analyzed using a potentiostat (VersaSTAT 3) while applying a voltage of −0.3 V and the change in signal between 3 and 7 seconds was determined. The result is shown in FIG. 12.

Figure 12:
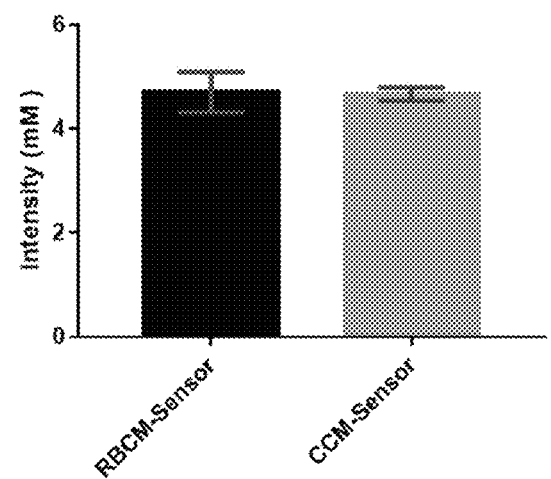
FIG. 12 shows a result of measuring signals for a biosensor containing red blood cell membrane (RBCM) as a filter and a biosensor containing cancer cell membrane (CCM) as a filter.

As seen from FIG. 12, both the red blood cell membrane (RBCM)-coated biosensor and the cancer cell membrane (CCM)-coated biosensor could detect glucose in the serum with high sensitivity.

Test Example 10. Confirmation of Stability of Biosensor

In order to investigate the actual applicability of the biosensor of the present disclosure, the stability in the air was investigated. Specifically, the change in current depending on different glucose concentrations was measured immediately after the biosensor of the present disclosure was prepared and 3 weeks after it was kept in a desiccator. The result is shown in FIG. 13.

Figure 13:
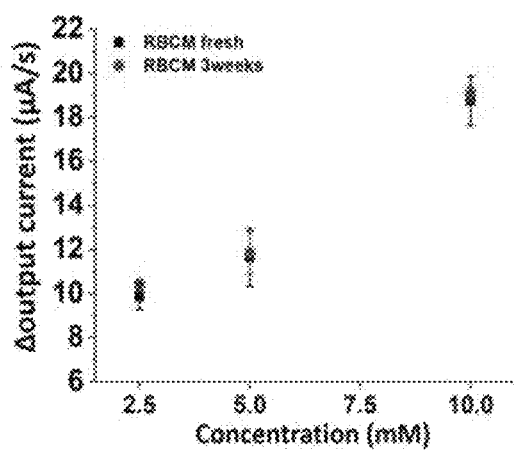
FIG. 13 shows a result of investigating the stability of a biosensor for measuring glucose of the present disclosure in the air.

As seen from FIG. 13, the biosensor of the present disclosure maintained the ability of allowing selective permeation of glucose and could effectively detect glucose without being significantly affected by contact with air. Because the cytoplasmic membrane filter unit according to the present disclosure is not significantly affected by the moisture in the air, it is highly applicable industrially.

To conclude, the biosensor of the present disclosure, which contains the cytoplasmic membrane filter unit allowing selective permeation of glucose in the biological sample, exhibits high glucose detection sensitivity as compared to the commercially available blood sugar measuring sensors and also exhibits high glucose detection specificity despite the addition of signal-interfering substances such as fructose, xylose, maltose, cysteine, ascorbic acid, uric acid, galactose, etc. In addition, because he cytoplasmic membrane filter unit contained in the biosensor for measuring glucose of the present disclosure is not significantly affected by the moisture in the air, it can be applied to various products such as a disposable blood sugar test strip or an attachable or implantable glucose measuring device.

What is claimed is:
1. A biosensor for measuring glucose, comprising:
a filter comprising a cytoplasmic membrane of a red blood cell for selectively permeating the glucose in a biological sample;
a sensor disposed under the filter and recognizing the permeated glucose; and
a reader comprising an electrochemical device connected to the sensor and reading a signal of the recognized glucose,
wherein the cytoplasmic membrane comprises a glucose transporter (GLUT) protein,
wherein the sensor comprises an enzyme using the permeated glucose as a substrate, and
wherein a thickness of the filter is about 220 nm.
2. The biosensor for measuring glucose in the biological sample according to claim 1, wherein the biological sample is one or more selected from a group consisting of blood, tears, urine and sweat.

3. The biosensor for measuring glucose in the biological sample according to claim 1, which further comprises an electron transport mediator disposed between the sensor and the reader converting an amount of the glucose recognized by the sensor into an electrical signal.

4. A kit for measuring glucose in a biological sample, comprising a biosensor, wherein the biosensor comprises:
   a filter comprising a cytoplasmic membrane of a red blood cell for selectively permeating the glucose in a biological sample;
   a sensor disposed under the filter and recognizing the permeated glucose; and
   a reader comprising an electrochemical device connected to the sensor and reading a signal of the recognized glucose,
   wherein the cytoplasmic membrane comprises a glucose transporter (GLUT) protein,
   wherein the sensor comprises an enzyme using the permeated glucose as a substrate, and
   wherein a thickness of the filter is about 220 nm.

5. A method for measuring a glucose level in a biological sample providing a biosensor and contacting a biological sample to the biosensor,
   wherein the biosensor comprises:
   a filter comprising a cytoplasmic membrane of a red blood cell for selectively permeating the glucose in the biological sample;
   a sensor disposed under the filter and recognizing the permeated glucose; and
   a reader comprising an electrochemical device connected to the sensor and reading a signal of the recognized glucose,
   wherein the cytoplasmic membrane comprises a glucose transporter (GLUT) protein,
   wherein the sensor comprises an enzyme using the permeated glucose as a substrate, and
   wherein a thickness of the filter is about 220 nm.

6. The biosensor for measuring glucose in the biological sample according to claim 1, wherein the enzyme is selected from the group consisting of glucose oxidase, glucose dehydrogenase (GDH), glucose hexokinase, cholesterol oxidase, glutamic oxaloacetic transaminase (GOT), glutamic pyruvic transaminase (GPT), and a combination thereof.

* * * * *